United States Patent [19]

Mochida et al.

[11] 4,308,026
[45] Dec. 29, 1981

[54] AGGLUTINATION INHIBITION IMMUNOASSAY FOR HAPTEN USING TWO DIFFERENTLY SENSITIZED PARTICLES

[75] Inventors: Ei Mochida, Tokyo; Nobuhisa Ogawa, Omiya; Hiroyuki Shinkai, Kawagoe; Takashi Kudo, Tokyo, all of Japan

[73] Assignee: Mochida Seiyaku Kabushiki Kaisha, Tokyo, Japan

[21] Appl. No.: 59,338

[22] Filed: Jul. 23, 1979

Related U.S. Application Data

[63] Continuation of Ser. No. 835,132, Sep. 21, 1977, abandoned.

[30] Foreign Application Priority Data

Sep. 29, 1976 [JP] Japan ............................. 51/0117027

[51] Int. Cl.$^3$ ............................................. G01N 33/54
[52] U.S. Cl. ................................... 23/230 B; 424/12; 23/915
[58] Field of Search ......................... 424/12; 23/230 B

[56] References Cited

U.S. PATENT DOCUMENTS

| | | | |
|---|---|---|---|
| 3,088,875 | 5/1963 | Fisk | 424/12 |
| 3,655,838 | 4/1972 | Price | 424/12 X |
| 3,766,162 | 10/1973 | Spector | 424/12 X |
| 3,862,302 | 1/1975 | Price | 424/12 |
| 3,879,262 | 4/1975 | Schuurs | 424/12 X |
| 3,904,475 | 2/1976 | Gross | 424/12 X |
| 4,026,879 | 5/1977 | Spector | 424/12 X |
| 4,031,117 | 6/1977 | Rao | 424/12 X |
| 4,036,823 | 7/1977 | Soares | 424/12 X |

OTHER PUBLICATIONS

Chemical Abstracts I, 75:107467h (1971).
Chemical Abstracts II, 80:68104u (1974).
"Methods in Immunology and Immunochemistry," C. A. Williams et al., eds., vol. III, pp. 427-434, Academic Press, New York, 1971.
"Principles of Immunology", 2nd Edition, N. R. Rose et al., eds., pp. 86-106, MacMillan Publishing Co., New York, 1979.

*Primary Examiner*—Sidney Marantz
*Attorney, Agent, or Firm*—Brisebois & Kruger

[57] ABSTRACT

An immunochemical process and the reagents for measuring hapten by using an agglutination inhibition reaction, anti-hapten antibody sensitized particles and a hapten-carrier conjugate which is capable of agglutinating said particles.

4 Claims, No Drawings

AGGLUTINATION INHIBITION IMMUNOASSAY FOR HAPTEN USING TWO DIFFERENTLY SENSITIZED PARTICLES

This is a continuation, of application Ser. No. 835,132, filed Sept. 21, 1977, now abandoned.

BACKGROUND OF THE INVENTION

Recently an increased importance has been attached to clinical testing or diagnosis in which a patient's pathological condition or prognosis is judged or the dose of medicine to be administered to him is determined, by measuring the urinary or the blood level of hapten such as a low-molecular physiologically active substance which is present in his body and its metabolites or a medicine administered to him and its metabolites.

The haptens to be measured in this clinical testing or diagnosis include; androgens such as testosterone, dehydroepiandrosterone, androsterone; glucocorticoids such as cortisone, cortisol, corticosterone; mineral corticoids such as aldosterone; progestogens such as progesterone; estrogenes such as estriol, estradiol; thyroid hormones such as thyroxine, triiodothyronin; prostaglandin; physiological active amines such as L-dopa, epinephrine, norepinephrine, histamine and their metabolites.

The medicines to be measured in this testing or diagnosis include: medicines whose dose should be determined with utmost caution and whose effects have a correlation with their concentration in the blood or urine, i.e., digitalis preparations; antibiotics such as tetracyclin; psychotropic agents such as amphetamine; narcotic agents such as morphine; blood-coagulating agents or anticoagulating agents.

The term "hapten" used in the present specification means a low-molecular physiological active substance present in the human body and its metabolite or a medicine administered to the human body and its metabolite, which alone is not capable of producing an antibody and, only when bound with a substance which in itself is an antigen such as protein, polysaccharide, glycoprotein, is capable of producing an antibody, (hereafter to be referred to simply as a carrier) and is capable of reacting with said antibody produced.

Usually haptens occur in traces and they exist in complexed or conjugated form in blood or urine which are complex compositions. Thus an intricate, time-consuming process is needed for their detection and measurement.

Haptens may be measured by conventional methods such as the physico-chemical process, the immunochemical process, and the competitive protein binding process.

In the physico-chemical process, the hapten complex or conjugate in blood or urine is hydrolyzed by means of acid, alkali or enzyme and after purification, applied to chromatography, etc., for measurement. The operation involved, however, is complicated and time-consuming; in the course of hydrolysis steroids vanish through decomposition in the case of certain steroids or the greater part of the steroids are adsorbed in the course of chromatography; and in consequence the amount of steroid eluted is so small that it is not measurable.

Meanwhile, the immunochemical process is superior in the specificity of the reaction and the sensitivity of the measurement to said physico-chemical one; and at present numerous techniques of measuring trace hapten in the human body are practically available such as the agglutination inhibition reaction process and radioimmunoassay (to be abbreviated to RIA hereafter). In said agglutination inhibition reaction process, a hapten-carrier conjugate which represents the same hapten as the hapten to be measured, as bound with a carrier (hereafter to be referred to as ANTIGEN) is employed as the antigen. An antibody to the hapten to be measured (hereafter to be called the ANTIBODY) is obtained from an antiserum produced from mammals such as guinea pigs, rabbits or sheep which have been immunized with the ANTIGEN. Then using said ANTIBODY and an ANTIGEN-sensitized particle which has been obtained by sensitizing blood cells or a fine particle of high-molecular latex (hereafter to be called particle), the agglutination reaction occurs between the two components. In this process the agglutination reaction inhibited by the presence of the hapten to be measured is utilized to obtain this measurement. Unlike said physico-chemical process, this is an extremely simple process which can measure the hapten existing as a complex or conjugate in the blood or urine without complicated operations such as hydrolysis or chromatography. The sensitivity of this process is about 100 ng/ml even when blood cells, i.e., an excellent particle or sensitizing ANTIGEN is adopted. Since most haptens which are known to be worth measuring in the human body occur in the range of 500 pg/ml-50 ng/ml, they have to be concentrated for successful measurement.

In the competitive protein binding process, instead of the antibody employed in RIA a hapten receptor or a binding protein present in the human body is employed. With a measured value well correlated to the biological activity exhibited by hapten, this process is found useful, but it has the drawbacks that only a few haptens such as estrogen, cortcosteroid, thyroid hormone have known receptors; but a complicated operation is needed for extraction and purification of these receptors and these receptors after extraction do not keep long.

SUMMARY OF THE INVENTION

It is an object of the present invention to provide a novel immunochemical process for measuring hapten. Another object of the invention is to provide the reagents for hapten measurement based on said novel process. These objects have been attained by use of a agglutination inhibition reaction, using an anti-hapten antibody sensitized particle and a hapten-carrier conjugate.

DETAILED EXPLANATION OF THE INVENTION

The immunochemical process of measuring hapten according to the present invention is different from the conventional process utilizing the agglutination inhibition reaction and it is characterized by virtue of its composition in that it gives an exceedingly good effect unobtainable from the conventional process.

In the conventional immunochemical measuring method using an ANTIGEN and an ANTIBODY, and ANTIGEN sensitized particle and an ANTIBOY are employed to measure the hapten by utilizing the effect of hapten to be measured inhibiting the agglutination of the ANTIGEN sensitized particle due to the ANTIBODY. In the case of the present invention using an ANTIBODY sensitized particle and an ANTIGEN not sensitized to the particle or an ANTIGEN sensitized to the particle, hapten is measured by utilizing the agglutination reaction of the ANTIBODY sensitized particle due to the ANTIGEN and agglutination inhibition reaction of hapten to be measured.

There are agglutination reactions (AR) and agglutination inhibition reactions (AIR) in the reaction system in which a particle is immunologically employed.

In a AR the antigen-antibody reaction occurs on the surface of each particle sensitized with antibodies, and the particles combine one with another through thus reacted antigens in the following manner:

I. 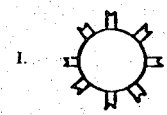 + 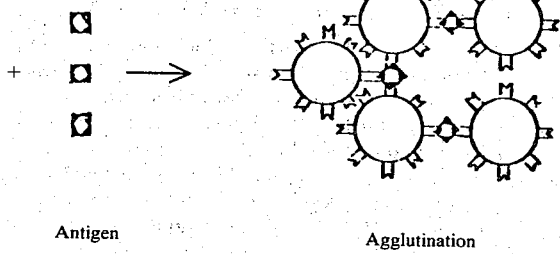

Antibody sensitized particle    Antigen    Agglutination

In the case of hapten, however, as shown in reaction II, no agglutination occurs because hapten does not make ANTIBODY sensitized particles combine with one another.

II.  + 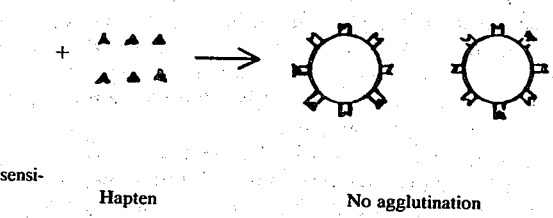

ANTIBODY sensitized particle    Hapten    No agglutination

In a AIR as shown in reaction III, antigens to be measured inhibit the agglutination which both antibodies and particles sensitized with antigens attempt. As shown in reaction IV, AIR also occur with hapten.

III.

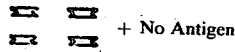 + No Antigen

Antibody

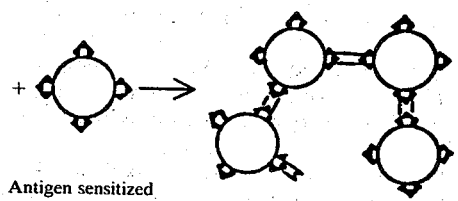

Antigen sensitized particle

 +  → 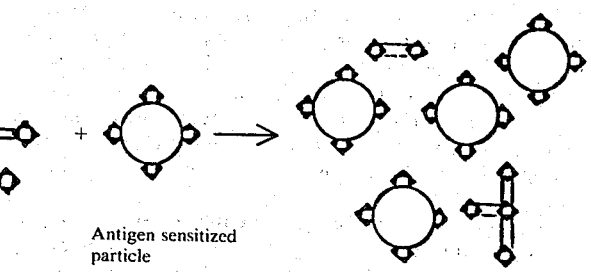

Antibody    Antigen      Antigen sensitized particle

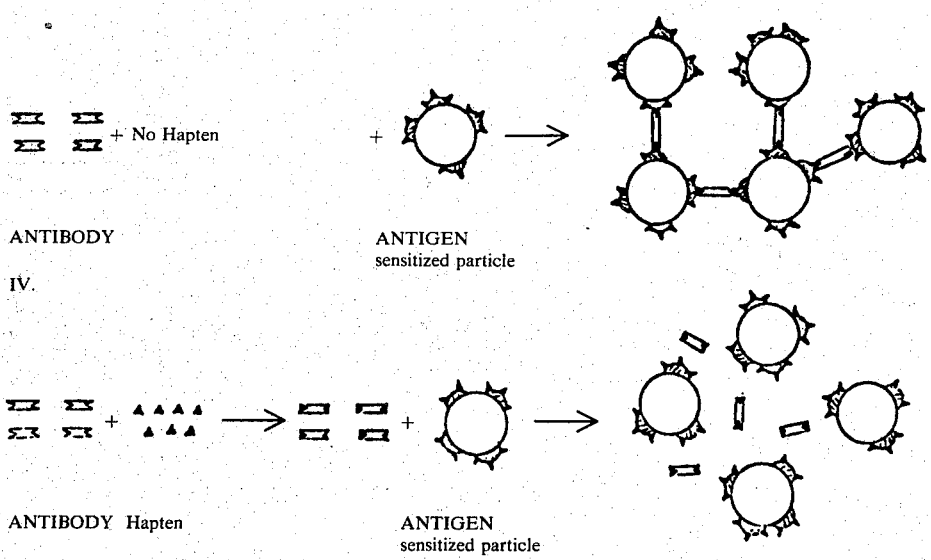

ANTIBODY     ANTIGEN sensitized particle

IV.

ANTIBODY   Hapten     ANTIGEN sensitized particle

Because of the low molecular weight of hapten in general, it is necessary to produce ANTIBODIES by immunizing an animal after hapten is changed into a carrier-conjugate. At the same time, it is difficult to sensitize hapten as it is to a carrier, so it is necessary to sensitize ANTIGEN to particles when measuring hapten with AIR.

Generally speaking, an antigen's molecular weight is high, and antibodies can be produced by immunizing an animal with an untreated antigen. Hapten is a kind of antigen, but, as mentioned above, it differs from ordinary antigens in many respects, such as in the process of producing its ANTIBODIES, in the process to conjugate it to a carrier, and in the reactivity on its ANTIBODIES.

Because of the reasons mentioned above, in most cases one is unable to employ the reaction system using ordinary immunological particles in measuring hapten. So far, therefore, AIR using particles sensitized with ANTIGENS has been employed as a sole reaction system to measure hapten.

The inventors of this invention, after long research, have discovered the new reaction system of AIR by newly adding the ANTIGEN as one of the factors consisting of the reaction system that hapten antigen to be measured inhibits agglutination which occurs between the particles sensitized with the ANTIBODIES and ANTIGENS as shown in reaction V.

Reactions V

Illustrate the agglutination inhibition reaction of this invention

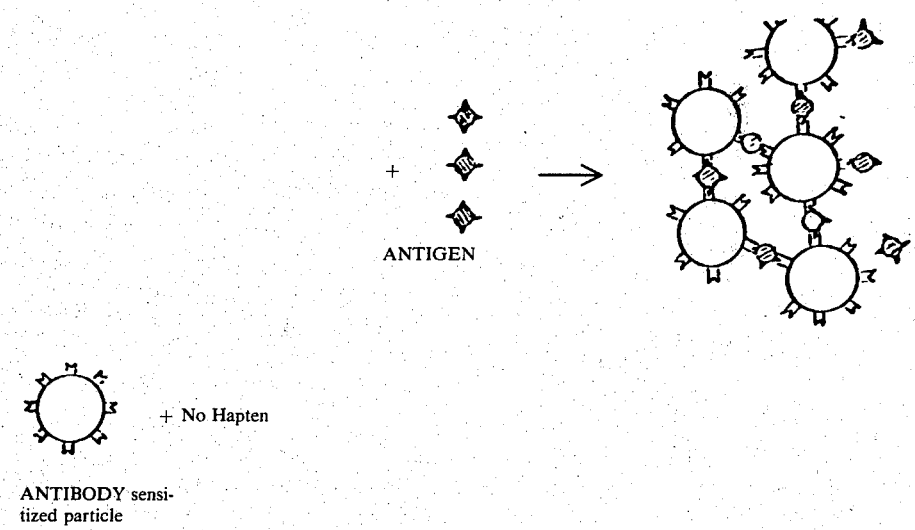

ANTIGEN

ANTIBODY sensitized particle

-continued
Reactions V

V.

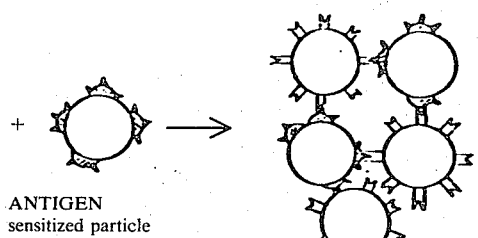

ANTIGEN
sensitized particle

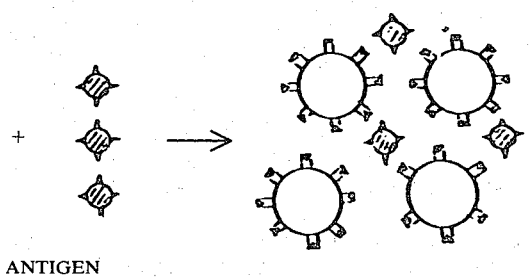

ANTIGEN

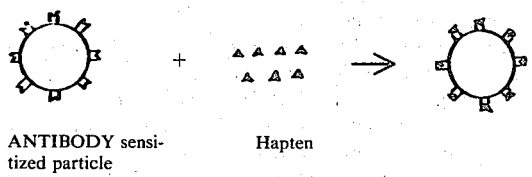

ANTIBODY sensi-      Hapten
tized particle

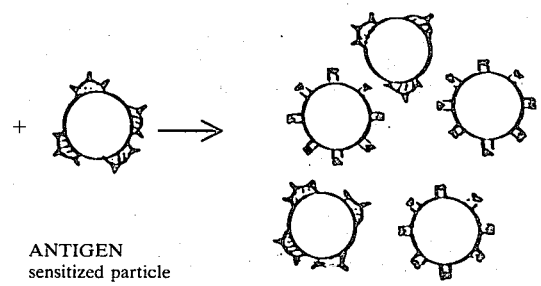

ANTIGEN
sensitized particle

For execution of the present invention, usually a given volume of the body fluid or excretion containing the hapten to be measured is sampled and this is used directly as a test solution or appropriately diluted to several levels of concentration and reaction is caused between a given volume of said test solution and a given volume of said ANTIBODY sensitized particle. Next a given volume of ANTIGEN is added to this reaction mixture and after a certain reaction time the agglutination pattern or the agglutination inhibition pattern is observed and from the dilution factor of the test solution and the sensitivity of measurement of this process the hapten content in the test solution is estimated.

The ANTIBODY to be employed in the present invention is obtained as follows: a carrier is bound with hapten by a known method; an anti-serum is obtained from an animal immunized by routine method with said hapten carrier conjugate (ANTIGEN) as antigen; and an antibody to hapten alone (ANTIBODY) is obtained by removing through absorption the antibodies to substances other than hapten, say, antibodies to the carrier and/or the conjugated site between the carrier and the hapten. Here anything may be taken as the carrier; good results will be obtained if having high antigenicity, say, bovine serum albumin (to be abbreviated to BSA), human serum albumin (HSA), bovine γ-globulin (BGG), tetanus toxoid, glutamic acid-lysine-tyrosine copolymer or pneumococcal polysaccharide is employed.

As the particle to be sensitized by the ANTIBOY and the ANTIGEN, fine-particle carriers normally used in immunochemical agglutination reaction or agglutination inhibition reaction such as blood cells, high molecular latex, kaolinite, bentonite, active charcoal can be used. For the purpose of sensitizing these particle the ANTIBODY or the ANTIGEN, a 0.001–1.0% solution of ANTIBODY or ANTIGEN and a 2–20% suspension of particle to be sensitized are blended in equal proportions to react together for 30–90 minutes at 25°–56° C.

The ANTIGEN to produce an ANTIBODY and the ANTIGEN to cause the agglutination reaction may be different from each other in the carrier portion and/or the conjugated site between the carrier and the hapten. Meanwhile the hapten in the ANTIGEN to produce an ANTIBODY and the hapten in the ANTIGEN to cause agglutination reaction is not necessarily confined to the same hapten to be measured; provided the specificity of measurement is retained, they may be different substances exhibiting an immunochemical cross-reaction.

The haptens to be measured in the present invention include, as mentioned above: androgens; estrogens; progestogens; corticoids; thyroid hormones; physiological active amines such as epinephrine, histamine, serotonin, and their metabolites; medicines such as morphine, luteinizing hormone-releasing hormone, diphenylhydantoin and their metabolites.

The above-mentioned composition of the present invention has the following features.

As compared with the conventional method, the present invention produces an exceedingly high sensitivity measurement. This high sensitivity, though its mechanism is not yet clear, is believed to come from the fact that, the ANTIBODY, which the particle has been sensitized with, acts as a multivalent bond.

This speculation is based upon the fact that the sensitivity of the measurement can be further increased, when an ANTIBODY sensitized particle and an ANTIGEN sensitized particle are used together. Meanwhile, in the present invention, judgement is easy, because the patterns of agglutination and agglutination inhibition are quite distinct; and this is also believed to be due to the ANTIBODY acting as a multivalent bond.

According to the present invention, which needs only a small amount of ANTIBODY and ANTIGEN, these substances can be economized. For instance, the consumption of a certain ANTIGEN, i.e., estriol glucuronide-BSA which is difficult to produce and accordingly very expensive can be reduced to about 1/100–1/1,000 of the amount required in the conventional method.

Unlike the conventional method, the present invention permits use of an ANTIBODY with a low titre. Generally speaking, the ANTIBODY is difficult to produce and especially difficult to produce one with a high titre. When an ANTIBODY with a low titre is employed, due to a non-specific agglutination reaction, the measurement itself cannot be executed, or even if it can be executed, its sensitivity of the measurement is low. According to the present invention, even with the use of an ANTIBODY with a low titre the sensitivity of the measurement does not become lower; moreover, since the ANTIBODY can be economized, when a good ANTIBODY is produced, the ANTIBODY can remain in use for a long time (namely, the same ANTIBODY is used for manufacturing a large number of the kits) and accordingly a kit for the invented process can be consistently manufactured with good quality.

In the present invention, depending on the kind, the level of hapten to be measured and on the purpose of the measurement, the sensitivity can be arbitrarily adjusted by controlling the amount of the ANTIBODY for sensitization of particles and/or the corresponding ANTIGENS, or selecting the combination of the batch of ANTIBODIES and the batch of ANTIGENS, or adding to the reaction system a substance such as HSA, BSA, RSA (rabbit serum albumin) or surfactant or combining several of these steps.

The amount of ANTIGEN, ANTIBODY and the sensitivity in the conventional method of measurement of urinary estrogen were compared with those of the method of the present invention. The results are shown in Table 1.

In Table 1, the ANTIBODY means an anti-estriol antibody and is produced by the animal immunized with estriol-16,17-dihemisuccinate-BSA. The ANTIGEN means estron-17-(o-carboxymethyl) oxime-BSA or estriol-16, 17-dihemisuccinate. As the particle to be sensitized with the ANTIBODY or the ANTIGEN, sheep's blood cells and polystyrene latex were employed.

TABLE 1

| Method | Particle | Amount of ANTIGEN (μg/test) | Amount of ANTIBODY (μg/test) | Sensitivity (μg/ml) | Time for measurement |
|---|---|---|---|---|---|
| Invented | Sheep's blood cell | $3 \times 10^{-4}$ | 3 | $2 \times 10^{-3}$ | 2 hr |
|  | Polystyrene latex | $3 \times 10^{-2}$ | 3 | $1 \times 10^{-2}$ | 5 min |
| Conventional | Sheep's blood cell | $4 \times 10^{-1}$ | 30 | $1 \times 10^{-1}$ | 2 hr |
|  | Polystyrene latex | 3 | 30 | $5 \times 10^{-1}$ | 5 min |

It is evident from Table 1, that the method of this invention is 50 times as sensitive in the estrogen measurement as the conventional method and it can reduce the amount of ANTIGEN to 1/100–1/1,300 and the amount of ANTIBODY to 1/10 of that in the conventional method.

When sheep's blood cells are employed as the particle for the ANTIGEN or the ANTIBODY, the measurement can be highly sensitive but takes a rather long time. When, however, polystyrene latex is employed, the sensitivity decreases to 1/5 but the time required can be shortened to 1/20. Thus a suitable particle can be chosen meeting the purpose of measurement.

Next, the distinctiveness of the agglutination and agglutination inhibition patterns between the invented method and the conventional method was compared. Various concentrations of estriol-16 α-glucuronide in glycine-buffer saline in Table 2 were measured by the invented method and the conventional method, using polystyrene latex as the particle for ANTIBODY or ANTIGEN.

In this comparison the sensitivity in both cases was adjusted to the same 10 μg/ml so that only the distinctiveness of the agglutination and agglutination inhibition patterns could be examined free from the influence of the sensitivity.

Agglutination and agglutination inhibition were judged by the following criteria by the naked eye observations:
- −: agglutination complete inhibition
- ±: not discriminable as agglutination or agglutination inhibition
- +: discriminable as agglutination by scrutiny
- + +: distinctive agglutination

TABLE 2

| Amount of estriole-16α-glucuronide (μg/ml) | 0 | 2.5 | 5.0 | 7.5 | 10.0 | 12.5 | 15.0 | 20.0 |
|---|---|---|---|---|---|---|---|---|
| Invented method | ++ | ++ | ++ | ++ | ++ | ± | − | − |
| Conventional method | ++ | ++ | + | + | + | ± | ± | − |

It is evident from Table 2, that in the conventional method the change of agglutination pattern from (++) to (−) requires a concentration difference of 17.5 μg/ml, i.e., from 2.5 μg/ml to 20 μg/ml, whereas in the method of this invention the pattern changes from (++) to (−) with a concentration difference of 5 μg/ml, i.e., from 10 μg/ml to 15 μg/ml. Thus with narrow ranges of (±), (+) where it is hard to judge whether the pattern is agglutination or agglutination inhibition, the invented method helps judgement and is found practically advantageous.

The present invention is illustrated by the following examples.

EXAMPLE 1—Measurement of estrogen in the urine of a normal woman (A) Synthesis of estriol-16,17-dihemisuccinate-BSA 600 mg of estriol-16,17-dihemisuccinate was dissolved in 12 ml of dioxan. To the solution of estriol-16,17-dihemisuccinate in dioxan was added 0.3 ml of tri-n-butylamine. After the mixture was cooled to about 11° C., 0.17 ml of isobutylchlorocarbonate was added, and then thoroughly agitated. Meanwhile, 40 ml of dioxan was added to the BSA solution which was dissolved 1.7 g of BSA in 40 ml of distilled water and adjusted to pH 12.0 by 1N-sodium hydroxide. Then, the mixture was cooled to 11° C. The former solution was mixed with this latter solution and the mixture was stirred for 4 hours. After then, the low-molecular substances such as the non-reacted estriol-16, 17-dihemisuccinate and tri-n-butylamine were separated by gel filtration (Sephadex G-25; trade name of Pharmacia Co. in Sweden). Estriol-16,17-dihemisuccinate-BSA was dialyzed against a distilled water containing 0.1% of sodium azide and lyophilized.

(B) Synthesis of estron-17-(O-carboxymethyl)oxime-BSA

Estron-17-(O-carboxymethyl)oxime-BSA was obtained by use of estron-17-(O-carboxymethyl)oxime and BSA in the same way as in (A).

(C) Production of anti-estriol-16,17-dihemisuccinate antibody 2 mg of estriol-16,17-dihemisuccinate-BSA in 1 ml of saline was emulsified with 1 ml of Freund's complete adjuvant and injected subcutaneously into rabbit. The injection was repeated five times every two weeks and after confirmation of an increase in the antibody titre, the rabbit was bled to obtain antiserum. After absorption by BSA, this antiserum was purified by a salting out process using anhydrous sodium sulfate to obtain anti-16,17-dihemisuccinate antibody.

(D) Preparation of anti-estriol-16,17-dihemisuccinate antibody-sensitized blood cells.

Sheep's blood cells fixed with formalin were washed with phosphate buffered saline (PBS) at pH 7.4; suspended in PBS at 4% concentration; mixed with an equal volume of 0.1% tannic acid in PBS; and then reacted at 56° C. for 30 minutes. Following the reaction, the blood cells were separated by centrifugation; washed with PBS and resuspended at 4% concentration. The suspension obtained was mixed with an equal volume of 0.02% of the anti-estriol-16,17-dihemisuccinate antibody solution obtained in (C) in PBS. After reaction at 56° C. for 30 minutes, it was washed with PBS and suspended at 2% concentration. The suspension of anti-estriol-16,17-dihemisuccinate antibody sensitized blood cells were obtained. Then 0.1 ml of this suspension was placed in an ampul and was lyophilized.

(E) Measurement of urinary estrogen

The urine of a normal woman was collected in every period of her menstrual cycle. The sample was diluted 5-, 10-, 20-, 40- and 80- folds in saline; and 0.1 ml of the dilutions was added in a round-bottomed ampul. The anti-estriol-16,17-dihemisuccinate antibody sensitized blood cells prepared in (D) was suspended with 0.3 ml of PBS per ampul. The whole amount of this suspension was added to the above mentioned round-bottomed ampul and mixed well. Then 0.1 ml of 5 ng/ml solution of the estron-(O-carboxymethyl) oxime-BSA obtained in (B) was added to the same ampul. The ampuls were then kept standing for two hours without vibration and a ring of sedimentation of blood cells was observed at the bottom of the ampul. The results are summarized in Table 3.

Since in the present example the sensitivity was adjusted to 2 ng/ml, the levels of urinary estrogen in each period were shown in the column (C) of Table 3.

TABLE 3

| (A) Menstrual cycle | (B) Dilution fold | | | | | (C) levels of urinary estrogen (ng/ml) |
|---|---|---|---|---|---|---|
| | ×5 | ×10 | ×20 | ×40 | ×80 | |
| 5th day pre-ovulatory | ++ | − | − | − | − | 10 |
| 9th day phase | ++ | − | − | − | − | 10 |
| 13th day ovulation | ++ | ++ | ++ | ++ | − | 80 |
| 17th day lutual phase | ++ | ++ | − | − | − | 20 |
| 23rd day | ++ | ++ | − | − | − | 20 |

Judgement
−: distinctive agglutination (indicating that the level of urinary estrogen is below the sensitivity)
++: agglutination completely inhibited (indicating that the level of urinary estrogen is above the sensitivity)

EXAMPLE 2—Measurement of urinary estrogen in pregnant women (A) Preparation of anti-estriol-16,17-dihemisuccinate antibody sensitized polystyrene latex Anti-estriol-16,17-dihemisuccinate antibody produced in Example (1-C) was dissolved in glycine buffered saline (GBS) at pH 8.2 to give the concentration of 0.08%; 5 ml of the solution obtained was mixed with 5 ml of 10% polystyrene latex suspension and the mixture was incubated at 45° C. for one hour. After then, the polystyrene latex separated by centrifugation and was suspended in 50 ml of GBS containing 0.1% BSA, thereby anti-estriol-16,17-dihemisuccinate antibody sensitized polystyrene latex was obtained.

(B) Preparation of estriol-16,17-dihemisuccinate-BSA tablets

Eight mg of estriol-16,17-dihemisuccinate-BSA in Example (1-A), 350 g of mannitol, 200 g of tartaric acid, 400 g of potassium bicarbonate and 50 g of acetylsalicylic acid were blended and compressed to tablets by the conventional way. Eight $\mu$g of estriol-16,17-dihemisuccinate-BSA was contained in each tablet obtained.

(C) Measurement of urinary estrogen

Three urine specimens of pregnant women were diluted 25-, 50-, 100- and 200 folds respectively. Each diluted urine specimen was dropped (each drop 0.025 ml) onto a slide glass using a titration pipette and a drop of GBS and a drop of the anti-estriol-16,17-dihemisuccinate antibody sensitized polystyrene latex obtained in (A) was dropped on this slide glass using titration pipettes. The three of those on the slide glass were mixed well; and a drop of 2 $\mu$g/ml solution of estriol-16,17-dihemisuccinate-BSA obtained by dissolving a tablet in (B) in 4 ml of distilled water was added; and after 3 minutes of mixing, the agglutination pattern of latex was observed by the naked eye under illumination.

The results are summarized in Table 4. In this example, in which the sensitivity was adjusted to 200 ng/ml, the levels of urinary estrogen in each sample were shown in the column (C) of Table 4, the judgement being the same as in Table 3.

TABLE 4

| (A) Number of urine specimen | (B) Dilution fold | | | | (C) Levels of urinary estrogen ($\mu$g/ml) |
|---|---|---|---|---|---|
| | × 25 | × 50 | × 100 | × 200 | |
| 1 | ++ | − | − | − | 5 |
| 2 | ++ | − | − | − | 5 |
| 3 | ++ | ++ | − | − | 10 |

EXAMPLE 3—Measurement of urinary pregnanediol of pregnant women (A) Synthesis of pregnanediol-3-glucuronide-BSA Pregnanediol-3-glucuronide-BSA was obtained by use of pregnanediol-3-glucuronide and BSA in the same way as in Example (1-A).

(B) Production of anti-pregnanediol-3-glucuronide antibody

Antiserum was obtained from a rabbit immunized with the pregnanediol-3-glucuronide-BSA obtained in (A) by the same method used in Example (1-C).

(C) Preparation of anti-pregnanediol-3-glucuronide antibody sensitized carboxylated polystyrene latex Anti-pregnanediol-3-glucuronide antibody sensitized carboxylated polystyrene latex was produced by the same method used in Example (2-A).

(D) Measurement of urinary pregnanediol

Using the dilutions of three urine specimens of pregnant women prepared in Example (2-B) and the pregnanediol-3-glucuronide-BSA and the anti-pregnanediol-3-glucuronide antibody sensitized carboxylated polystyrene latex obtained in (A) and (C), the level of urinary pregnanediol was determined in the same way as in Example (2-B). The results are summarized in Table 5.

In this example, in which the sensitivity was adjusted to 200 ng/ml, the levels of urinary pregnanediol of pregnant women were shown in column (C) of Table 5.

TABLE 5

| (A) Number of urine specimen | (B) Dilution fold | | | | (C) Levels of urinary pregnanediol ($\mu$g/ml) |
|---|---|---|---|---|---|
| | × 25 | × 50 | × 100 | × 200 | |
| 1 | ++ | − | − | − | 5 |
| 2 | ++ | ++ | − | − | 10 |
| 3 | ++ | ++ | ++ | − | 20 |

Judgement
− : distinctive agglutination (indicating that the level of urinary pregnanediol is below the sensitivity)
++ : Agglutination completely inhibited (indicating that the level of urinary pregnanediol is above the sensitivity)

EXAMPLE 4—Measurement of cortisol in serum (A) Synthesis of cortisol-21-hemisuccinate-BSA Using cortisol-21-hemisuccinate and BSA, cortisol-21-hemisuccinate-BSA was obtained in the same way as in Example (1-A).

(B) Synthesis of estradiol-17$\beta$-hemisuccinate-BSA

Estradiol-17$\beta$-hemisuccinate-BSA was obtained by use of estradiol-17$\beta$-hemisuccinate and BSA in the same way as in Example (1-A).

(C) Production of anti-cortisol antibody

Antiserum was obtained from a rabbit immunized with the cortisol-21-hemisuccinate-BSA obtained in (A) in the same way as in Example (1-C). This anti-serum was absorbed by the estradiol-17$\beta$-hemisuccinate-BSA obtained in (B) and then purified by salting out with anhydrous sodium sulfate, thereby obtaining an anti-cortisol antibody.

(D) Preparation of anti-cortisol antibody sensitized blood cells

The anti-cortisol antibody obtained in (C) was submitted to the same process as in Example (1-D) to obtain anti-cortisol antibody sensitized blood cells.

(E) Measurement of cortisol in serum

Five serum samples of a healthy man were heated at 70° C. for ten minutes; then respectively diluted 20-, 30-, 40-, 60- and 80- folds in saline; and 0.1 ml of the diluted urine was added to a round-bottomed ampul. The anti-cortisol antibody sensitized blood cells prepared in (D) was suspended with 0.3 ml of PBS per ampul. The whole amount of this suspension was added to said round-bottomed ampul and mixed well. Then 0.1 ml of 10 ng/ml solution of cortisol-21-hemisuccinate-BSA obtained in (A) was added to said ampul. The ampuls were then kept standing for two hours without vibration and a ring of sedimentation of blood cells was observed at the bottom of the ampul. The results are summarized in Table 6.

Since in this example with the sensitivity adjusted to 3 ng/ml, the levels of cortisol in each serum were shown in the column (C) of Table 6.

TABLE 6

| (A) Number of serum | (B) Dilution fold | | | | | (C) Levels of cortisol in serum (ng/ml) |
|---|---|---|---|---|---|---|
| | × 20 | × 30 | × 40 | × 60 | × 80 | |
| 1 | ++ | ++ | − | − | − | 90 |
| 2 | ++ | − | − | − | − | 60 |
| 3 | ++ | − | − | − | − | 60 |
| 4 | ++ | ++ | ++ | − | − | 120 |
| 5 | ++ | ++ | − | − | − | 90 |

Judgement
− : distinctive agglutination (indicating that the level of cortisol in serum is below the sensitivity)
++ : agglutination completely inhibited (indicating that the level of cortisol in serum is above the sensitivity)

EXAMPLE 5—Measurement of serotonin

(A) Synthesis of serotonin-p-aminophenylalanine-BSA 50 mg of DL-p-aminophenylalanine was dissolved in 5 ml of distilled water and 50 mg of BSA and 50 mg of 1 ethyl-3-(3-dimethylaminopropyl) carbodiimide were added to the solution. After agitation, the mixture was allowed to stand overnight. The reactant was dialyzed against distilled water and adjusted to pH 1.5. Thereto was added 100 mg of sodium nitrite in 1 ml of distilled water and further 50 mg of ammonium sulfamate in distilled water, the reactant was adjusted to pH 8.0. After adding to the reactant, 10 ml of 0.1 M-borate buffer solution containing 100 mg of creatinine sulfate of serotonin, it was agitated overnight in a cold, dark place. Serotonin-p-aminophenylalanin-BSA was obtained by dialysis against distilled water.

(B) Production of anti-serotonin antibody

250 μg of serotonin-p-aminophenylalanin-BSA in 0.5 ml of saline was emulsified with equal volume of Fredund's complete adjuvant; and by the same operation as in Example 1-(C), antiserum was obtained. This antiserum was absorbed by DL-p-aminophenylalanine-BSA, i.e., an intermediate product in the synthesis of serotonin-p-aminophenylalanine-BSA in (A) and purified by a salting out process using anhydrous sodium sulfate to obtain anti-serotonin antibody.

(C) Preparation of anti-serotonin antibody sensitized blood cells

Using the anti-serotonin antibody obtained in (C), anti-serotonin antibody sensitized blood cells were prepared in the same way as in Example 1-(D).

(D) Measurement of serotonin

Serotonin (Wako-junyaku K. K) was dissolved in saline and in urine no content of serotonin to different concentrations as listed in Table 7, and 0.1 ml each of the solution was added into a round-bottomed ampul. The anti-serotonin antibody sensitized blood cells prepared in (C) were suspended with 0.3 ml of PBS per ampul. The whole amount of this suspension was added to the above mentioned round-bottomed ampul and mixed well. Then 0.1 ml of 50 ng/ml solution of serotonin-p-aminophenylalanine-BSA obtained in (A) was added to said ampul. The ampuls were then kept standing for two hours without agitation and a ring of sedimentation of blood cells was observed at the bottom of the ampul. The results are summarized in Table 7.

The sensitivity in this example was 50 ng/ml and unaffected by the urine content.

TABLE 7

| (A) serotonin diluent | (B) Serotonin concentration μg/ml | | | | |
|---|---|---|---|---|---|
| | 0 | 0.025 | 0.05 | 0.10 | 0.20 |
| saline | − | − | ++ | ++ | ++ |
| urine containing no serotonin | − | − | ++ | ++ | ++ |

Judgement
− : distinctive agglutination (indicating that the level of serotonin is below the sensitivity)
++ : Agglutination completely inhibited (indicating that the level of serotonin is above the sensitivity)

EXAMPLE 6—Measurement of luteinizing hormone-releasing hormone

(A) Synthesis of lubeinizing hormone-releasing hormone-RSA

A solution of 40 mg of luteinizing hormone-releasing hormone (LH-RH) in 1 ml of saline was mixed with 1 ml of 5% RSA solution. 1 ml of 50% pyridine solution of 200 mg 1-cyclohexyl-3-[2-morpholinyl-(4)-ethyl]-carbodiimide metho-p-toluene sulfonate was added to this mixture, followed by agitation for 1 hour at room temperature. LH-RH-RSA was obtained by desalting with gel filtration (Sephadex G-25) and then by dialysis against PBS.

(B) Production of anti-LH-RH antibody 20 mg of LH-RH was dissolved in 1 ml of saline. 4 ml of 50% polyvinylpyrrolidone in saline was added to the solution, followed by agitation for two hours. After agitation, the mixture was emulsified with 5 ml of Freund's complete adjuvant and by the same operation as in Example 1-(C), anti-LH-RH antibody was obtained.

(C) Preparation of anti-LH-RH antibody sensitized blood cells

Using the anti-LH-RH antibody obtained in (B), anti-LH-RH antibody sensitized blood cells were prepared in the same process as in Example 1-(D).

(D) Measurement of LH-RH in blood

The concentration of LH-RH in the blood of a patient with malfunctioning of hypothalamo-hypophysial system who had been intravenously injected with 100 μg of LH-RH was measured. His serum was collected before injection and 2-, 5-, 10-, 30- and 60 minutes after the injection and it was diluted respectively 20-, 30-, 40-, 50- and 100 folds; and 0.1 ml of each dilution was added to a round-bottomed ampul. The anti-LH-RH antibody sensitized blood cells prepared in (C) was suspended with 0.3 ml of PBS per ampul. The whole amount of this suspension was added into the above mentioned round-bottomed ampul and mixed well. Then 0.1 ml of 5 ng/ml PBS solution of LH-RH-RSA obtained in (A) was added into the same ampul. The ampuls were then kept standing for two hours without vibration and a ring of sedimentation of blood cells was observed at the bottom of the ampul. The results are summerized in Table 8. In this example with the sensitivity adjusted to 1 ng/ml, the LH-RH content in each serum were shown in the column (C) of Table 8.

TABLE 8

| (A) Serum examined | (B) Dilution fold | | | | | (C) Levels of LH-RH in Serum (ng/ml) |
|---|---|---|---|---|---|---|
| | × 20 | × 30 | × 40 | × 50 | × 100 | |
| before injection of LH-RH | − | − | − | − | − | less than 20 |
| 2 min. after injection | ++ | ++ | ++ | − | − | 40 |
| 5 min. | ++ | − | − | − | − | 20 |
| 10 min. | − | − | − | − | − | less than 20 |
| 30 min. | − | − | − | − | − | less than 20 |
| 60 min. | − | − | − | − | − | less than 20 |

Judgement
− : distinctive agglutination (indicating that the level of LH-RH is below the sensitivity)
++ : agglutination completely inhibited (indicating that the level of LH-RH is above the sensitivity)

EXAMPLE 7—Measurement of diphenylhydantoin (A) Synthesis of 5-(p-carboxymethoxyphenyl)-5-phenylhydantoin 400 mg of 5-(p-hydroxyphenyl)-5-phenylhydantoin in 4 ml of absolute ethanol was mixed with 140 mg of chloroacetic acid in 3.5 ml of 1 N-potassium hydroxide ethanol solution and then the mixture was refluxed for 22 hours. After cooled, the mixture was acidified with 0.33 ml of 5 N-hydrochloric acid, followed by distillation to remove the ethanol. Then 20 ml of distilled water was added and the pH value was adjusted to 1.0-2.0 with 5 N-hydrochloric acid. The solution obtained was extracted four times with 5 ml of ethyl acetate and dried with anhydrous sodium sulfate. Then it was dissolved in 2 ml of chloroform-methanol (2:1, v/v) solution and the solution was fractionated through a 2.0×40 cm silica gel column. The second fraction was collected. 5-(p-carboxymethoxyphenyl)-5-phenylhydantoin (CMPPH) was obtained by evaporating the second fraction and dried on calcium chloride under vacuo.

(B) Synthesis of CMPPH-BGG

CMPPH-BGG was obtained by use of CMPPH and BGG in the same way as in Example 1-(A). Thereby BGG for synthesis was consumed three times as much as BSA consumed in 1-(A).

(C) Production of anti-CMPPH antibody

Using CMPPH-BGG obtained in (B), anti-CMPPH antibody was obtained in the same way as in Example 1-(C).

(D) Preparation of anti-CMPPH antibody sensitized blood cells

Anti-CMPPH antibody sensitized blood cells were produced by the same process used in Example 1-(D).

(E) Preparation of CMPPH-BGG sensitized blood cells

Using CMPPH-BGG instead of anti-CMPPH antibody, CMPPH-BGG sensitized blood cells were obtained by the same process as in Example 1-(D).

(F) Measurement of diphenylhydantoin in blood

The levels of diphenylhydantoin in the serum of a patient administered with diphenylhydantoin was measured. For measurement, his serum was diluted 10-, 20-, 40-, 60- and 80 folds and 0.1 ml of each dilution was added into a round-bottomed ampul. The anti-CMPPH antibody sensitized blood cells prepared in (D) was suspended with 0.2 ml of PBS per ampul. The whole amount of this suspension was added to the above mentioned round-bottomed ampul and mixed well. Then the CMPPH-BGG sensitized blood cells prepared in (E) were suspended with 0.2 ml of PBS per ampul. The whole amount of this suspension was also added to the round-bottomed ampul and mixed well. The ampuls were then kept standing for 2 hours without vibration and a ring of sedimentation of blood cells was observed at the bottom of the ampul. The results are summarized in Table 9.

In this example, in which the sensitivity was adjusted to 1 μg/ml, the levels of diphenylhydantoin in each serum were shown in the column (C) of Table 9.

TABLE 9

| (A) Number of serum | (B) Dilution fold | | | | | (C) Levels of diphenylhydantoin in serum (μg/ml) |
|---|---|---|---|---|---|---|
| | × 10 | × 20 | × 40 | × 60 | × 80 | |
| 1 | ± | − | − | − | − | less than 10 |
| 2 | ++ | ++ | ++ | − | − | 40 |
| 3 | + | ± | − | − | − | 10-20 |
| 4 | − | − | − | − | − | less than 10 |
| 5 | ++ | ++ | ++ | ± | − | 40-60 |

Judgement
−, ± : distinctive agglutination or indistinctive agglutination (indicating that the level of diphenylhydantoin in serum is below the sensitivity)
+, ++ : agglutination completely inhibited (indicating that the level of diphenylhydantoin is above the sensitivity)

What is claimed is:

1. An agglutination inhibition immunoassay for measuring the presence or level of a hapten in a sample comprising
   (a) mixing with said sample a quantity of antibody-sensitized particles, said antibody being reactive with the hapten under assay,
   (b) mixing with the mixture resulting from step (a) a quantity of antigen-sensitized particles, said antigen being reactive with said antibody; and
   (c) correlating the agglutination or lack thereof with the presence or level of said hapten in said sample.

2. The immunoassay of claim 1 wherein said antigen is a hapten-carrier conjugate.

3. The immunoassay of claim 1 wherein said particles are selected from the group consisting of blood cells, high molecular weight latex, kaolinite, bentonite and active charcoal.

4. The immunoassay of claim 2 in which the carrier of the hapten-carrier conjugate is selected from the group consisting of bovine serum albumin, human serum albumin, bovine gamma-globulin, tetanus toxoid, glutamic acid-lysine-tyrosine copolymer and pneumococcal polysaccharide.

* * * * *